United States Patent
Sutanto et al.

(10) Patent No.: US 12,059,542 B2
(45) Date of Patent: Aug. 13, 2024

(54) SYSTEM AND METHOD FOR VALVE CONTROL

(71) Applicant: Medtronic PS Medical, Inc., Fort Worth, TX (US)

(72) Inventors: Jemmy Sutanto, Louisville, CO (US); David A. Ruben, Louisville, CO (US); James Wasson, Louisville, CO (US); Shilpika Chowdhury, Louisville, CO (US); Mark E. Henschel, Louisville, CO (US)

(73) Assignee: Medtronic PS Medical, Inc., Minneapolis, MN (US)

( * ) Notice: Subject to any disclaimer, the term of this patent is extended or adjusted under 35 U.S.C. 154(b) by 850 days.

(21) Appl. No.: 16/944,466

(22) Filed: Jul. 31, 2020

(65) Prior Publication Data
US 2022/0032018 A1  Feb. 3, 2022

(51) Int. Cl.
*A61M 27/00* (2006.01)
*A61M 39/22* (2006.01)
*F16K 99/00* (2006.01)

(52) U.S. Cl.
CPC .......... *A61M 27/006* (2013.01); *A61M 39/22* (2013.01); *F16K 99/0023* (2013.01); *F16K 99/0042* (2013.01); *A61M 2039/226* (2013.01); *A61M 2205/3331* (2013.01); *F16K 2099/0088* (2013.01)

(58) Field of Classification Search
CPC .... A61M 2039/226; A61M 2205/0244; A61M 2205/3331; A61M 27/006; A61M 39/22; F16K 2099/0088; F16K 99/0023; F16K 99/0042
See application file for complete search history.

(56) References Cited

U.S. PATENT DOCUMENTS

| | | | |
|---|---|---|---|
| 3,924,635 A | 12/1975 | Hakim | |
| 4,387,715 A | 6/1983 | Hakim et al. | |
| 4,595,390 A | 6/1986 | Hakim et al. | |
| 4,714,458 A | 12/1987 | Hooven | |
| 5,643,195 A * | 7/1997 | Drevet | G05D 16/2086 604/9 |
| 6,391,019 B1 | 5/2002 | Ito | |
| 6,439,538 B1 * | 8/2002 | Ito | A61M 27/006 251/234 |
| 7,025,324 B1 | 4/2006 | Slocum et al. | |

(Continued)

FOREIGN PATENT DOCUMENTS

| | | |
|---|---|---|
| CN | 107854773 A | 3/2018 |
| EP | 0982048 A1 | 3/2000 |

(Continued)

OTHER PUBLICATIONS

International Search Report and Written Opinion regarding Application No. PCT/US2021/043832, mailed May 16, 2022.

(Continued)

*Primary Examiner* — Kai H Weng
(74) *Attorney, Agent, or Firm* — Harness, Dickey & Pierce, P.L.C.

(57) ABSTRACT

Disclosed is a system including a flow control assembly. The system may include a flow regulating shunt system, for various purposes. The flow control assembly may be controlled according to selected parameters and methods.

15 Claims, 7 Drawing Sheets

(56) References Cited

U.S. PATENT DOCUMENTS

| | | | |
|---|---|---|---|
| 7,618,391 B2* | 11/2009 | Madsen | F15C 5/00 604/9 |
| 9,629,987 B2 | 4/2017 | Anand et al. | |
| 2009/0005720 A1 | 1/2009 | Ludin et al. | |
| 2015/0346732 A1 | 12/2015 | Chappel | |
| 2019/0126018 A1 | 5/2019 | Browd et al. | |

FOREIGN PATENT DOCUMENTS

| | | |
|---|---|---|
| EP | 1008765 A2 | 6/2000 |
| EP | 1092450 A1 | 4/2001 |
| EP | 1852615 A2 | 11/2007 |
| EP | 2008683 A1 | 12/2008 |
| JP | 2001242024 A | 9/2001 |
| WO | 9509989 A1 | 4/1995 |
| WO | 2013096340 A1 | 6/2013 |

OTHER PUBLICATIONS

International Search Report and Written Opinion regarding International Application No. PCT/US2021/043658, dated Dec. 7, 2021.

* cited by examiner

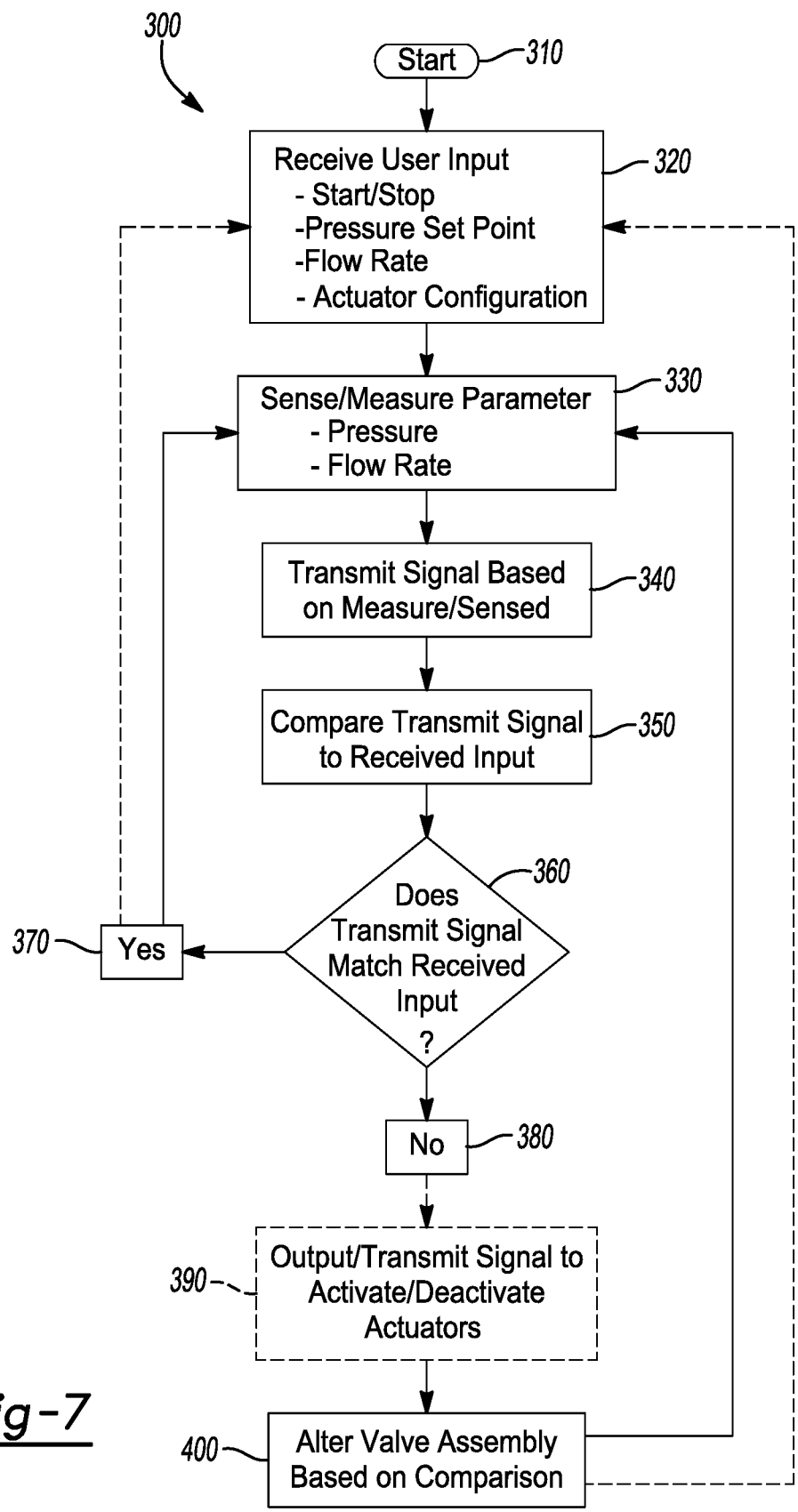

SYSTEM AND METHOD FOR VALVE CONTROL

CROSS-REFERENCE TO RELATED APPLICATIONS

This application includes subject matter similar to that disclosed in concurrently filed U.S. patent application Ser. No. 16/944,440 filed Jul. 31, 2020. The entire disclosure of the above application is incorporated herein by reference.

FIELD

The subject disclosure relates to a valve assembly, and particularly to a valve assembly and method therefore.

BACKGROUND

This section provides background information related to the present disclosure which is not necessarily prior art.

A system may be used to treat a selected or various conditions of a subject. The subject, for example a human subject, may be treated for hydrocephalous. Hydrocephalous may be caused due to an overproduction, under absorption, or blockage of outflow of cerebral spinal fluid (CSF) from a ventricle in a brain of a subject. Hydrocephalous, therefore, may cause various conditions in the subject. It may be desirable to treat the hydrocephalous with a shunt system to allow for drainage of the CSF from the ventricle to a different area of the subject to treat or alleviate the undesired conditions of the subject.

SUMMARY

This section provides a general summary of the disclosure, and is not a comprehensive disclosure of its full scope or all of its features.

A shunt system may be implanted into a subject as a therapy for hydrocephalous. The shunt system may include an inlet and an outlet to shunt or direct fluid away from a first area to a second area of the subject. In various embodiments, an inlet catheter may be implanted into a ventricle of the subject and an outlet catheter may be positioned in a distal area, such as a peritoneum and/or vasculature of the subject. The shunt system may further include a flow control system.

The flow control system may include a valve assembly. The valve assembly may have an opening or cracking pressure that will allow fluid to flow through the valve system at a selected pressure. The valve system may include a valve seat and selected mechanism to select or control a cracking pressure of the valve body.

The flow control assembly may include various portions, such as microelectromechanical systems (MEMS) to operate on the valve body and seat. The MEMS system may be controlled by various control portions in the flow control assembly. The flow control assembly, therefore, may be a valve assembly that is mechanically operated with the MEMS system.

Further, the control system may include one or more processors and a selected memory that may operate or control the MEMS system. Accordingly, the valve flow control may be controllable, such as autonomously or semi-autonomously, controlled. Further, one or more feedback loops, which may be opened or a closed feedback loop, may be used to assist in controlling the valve assembly. Therefore, the flow control assembly may include one or more valve portions that may be used to control the valve assembly for operation of a shunt system.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 7 is a flow chart of an operation of a valve assembly, according to various embodiments.

Corresponding reference numerals indicate corresponding parts throughout the several views of the drawings.

DETAILED DESCRIPTION

Example embodiments will now be described more fully with reference to the accompanying drawings.

Figure 1:
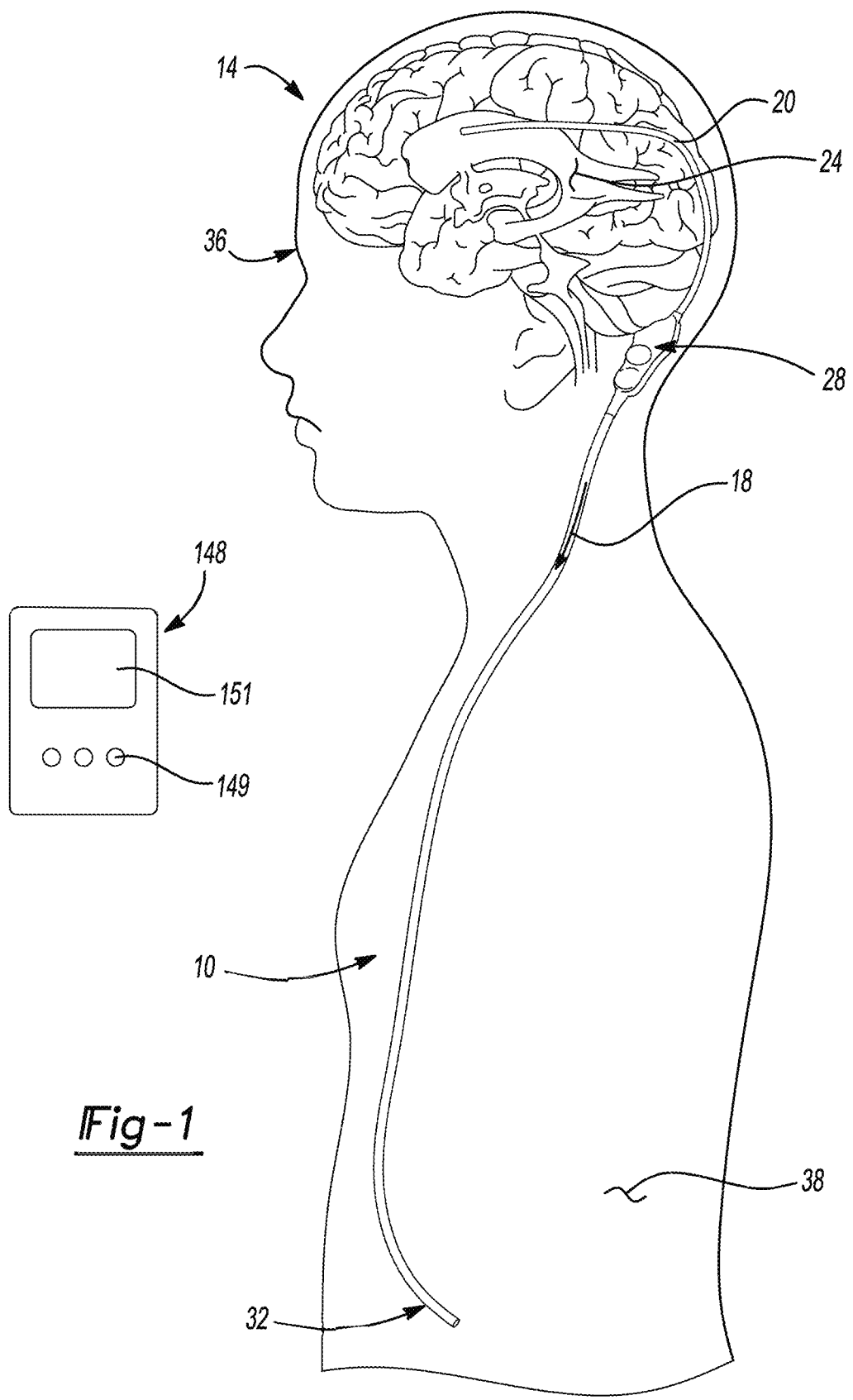
FIG. 1 is a schematic environmental view of a shunt and system positioned in a subject, according to various embodiments.

FIG. 1 includes an illustration of a fluid directing or shunt system 10. The shunt system 10 may be positioned or implanted within a subject 14, such as a human subject. The shunt system 10 may shunt or direct a fluid to flow along the shunt system 10, such as in the direction of arrow 18. The shunt system 10 may include a catheter 20, which may be an inlet catheter, positioned within a ventricle 24 in the subject 14. As is generally understood by one skilled in the art, the inlet catheter 20 may be positioned (i.e. implanted) in the ventricle 24 to allow the fluid to be drained away from the ventricle 24. The shunt system 10 may further include a selected flow control system 28 and an outlet catheter 32.

The selected flow control system 28 may be implanted in the subject 14 in an appropriate position. In various embodiments, the selected flow control system 28 may be implanted generally near a skull 36 of the subject 14, a torso 38 of the subject 14, or any other appropriate location. It is understood that the inlet catheter 20 may be connected to the selected flow control system 28 as is the outlet catheter 32.

The outlet catheter 32 may extend from the selected flow control system 28 to a selected location, such as a peritoneal cavity in the torso 38 of the subject 14. The inlet catheter 20, the selected flow control system 28, and the outlet catheter 32 may generally be understood to be a shunt system 10. The shunt system 10 may be useful as a hydrocephalus shunt system. The shunt system 10 may be entirely implanted in the subject 14.

Figure 3:
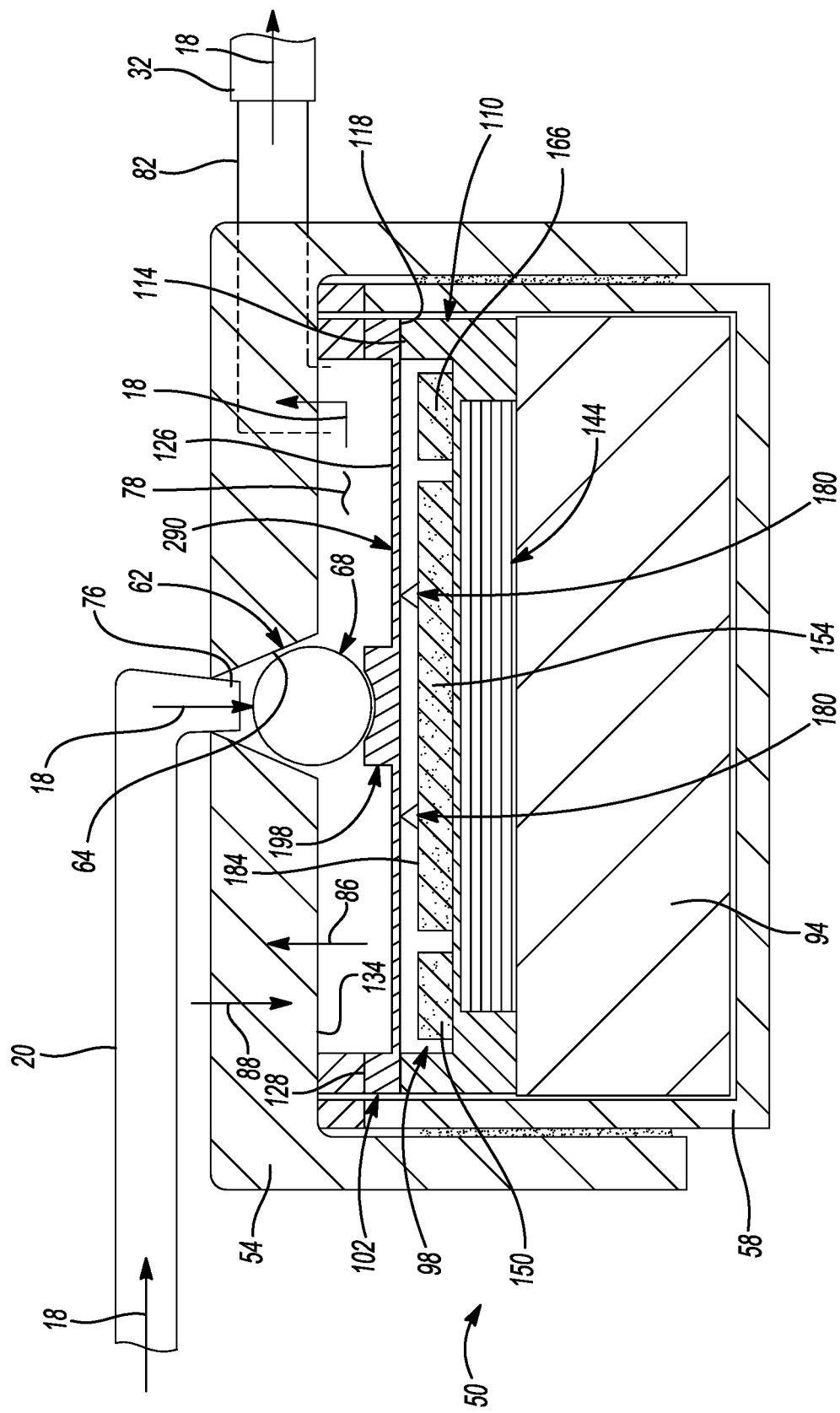
FIG. 3 is a cross-sectional view taken along lines 3-3 of FIG. 2.

The fluid may flow in the direction of arrow 18 into and through the inlet catheter 20, through the selected flow control system 28, and through the outlet catheter 32. The fluid may then drain or pass through the outlet catheter 32 into the peritoneal cavity, or any other appropriate location, of the subject 14. The fluid may be cerebral spinal fluid (CSF) that is produced in the ventricle 24. The shunt system 10 may be implanted to assist in treating hydrocephalus in the subject 14. It is understood that the outlet catheter 32 may be positioned within the subject 14 in an appropriate location to allow for draining of the CSF from the ventricle 24 to an appropriate location, such as one with high blood flow. Accordingly, as illustrated in FIG. 3, the inlet catheter 20, the selected flow control system 28, and the outlet catheter 32 may be implanted or positioned in the subject 14 as a CSF shunt system.

Figure 2:
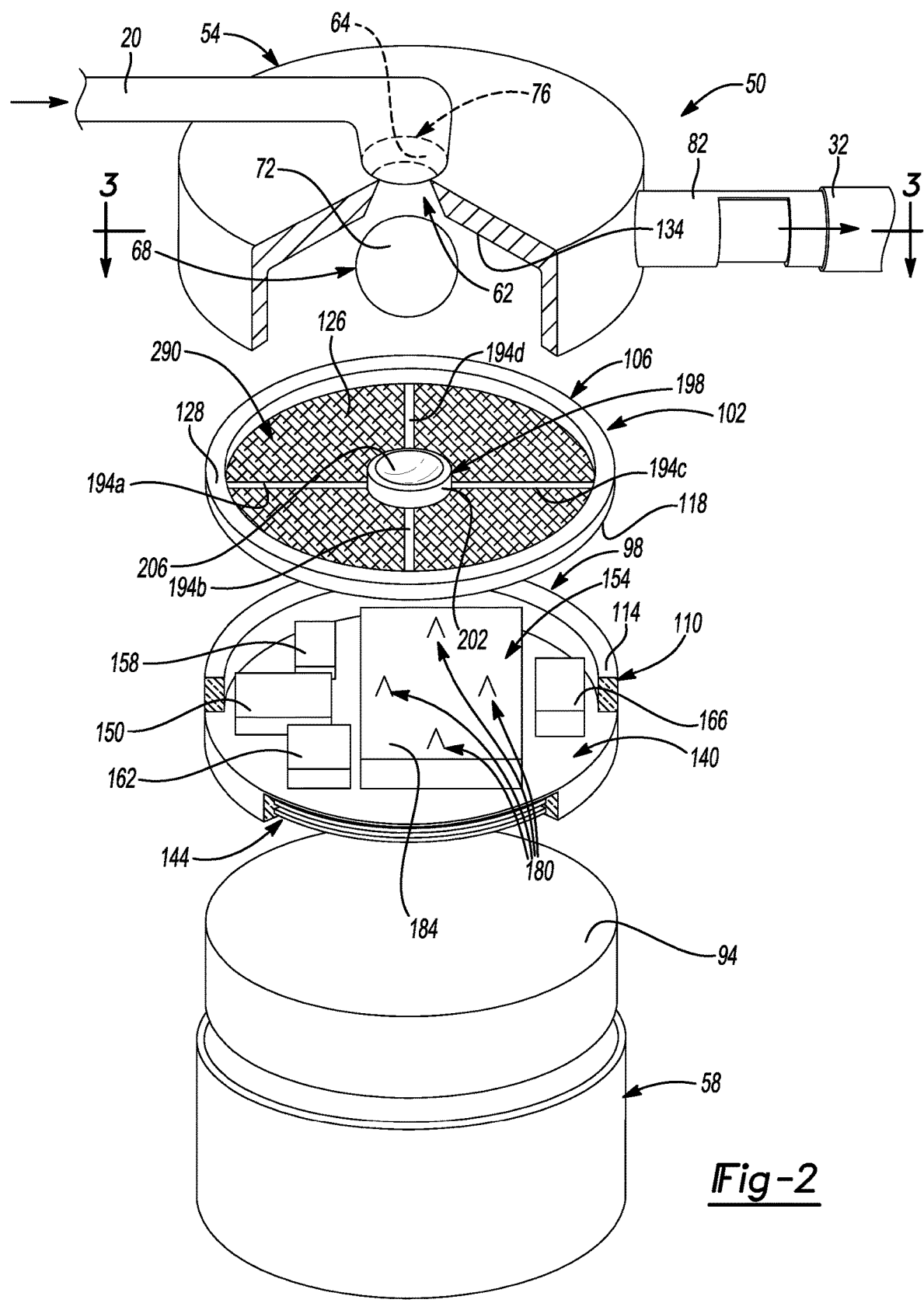
FIG. 2 is an exploded diagrammatic view of a valve assembly, according to various embodiments.

As discussed above, the shunt assembly 10 may include the flow control assembly 28. In various embodiments, the flow control assembly may include a valve assembly 50. With reference to FIGS. 2 and 3, the valve assembly 50 is illustrated. The valve assembly 50 may be incorporated into the flow control assembly 28, including with other portions therein, such as inlet and outlet coverings, filters, and the like, or may be included as the only portion of the flow control assembly 28. Accordingly, the valve assembly 50 may be understood to be the flow control assembly or system 28, as discussed above, or at least a portion thereof.

The valve assembly 50, therefore, may be provided as the flow control assembly 28 for controlling a flow through the shunt assembly 10 according to various embodiments. The valve assembly 50 may include the portions discussed further herein, and may be operated, as also discussed herein, in various embodiments.

The valve assembly 50 may generally include various portions, such as a first valve body or enclosure 54, that may also be referred to as a cap. The valve body 54 may include the cap or other removable portion relative to additional portions, such as a base or lower enclosure or body portion 58. The valve cap 54 may include one or more portions, such as a valve seat or seal area 62 that forms or defines a seal surface 64. The seal surface 64 may be engaged by a sealing member, such as a ball 68. The ball or sealing member 68 may include an external surface 72 that is formed to mate with the sealing surface or ring 64. The valve assembly 50, therefore, may seal the sealing member 68 into the sealing surface 64 to stop a flow through the valve assembly 50.

The valve assembly 50 may include the inlet 20 that engages or seals to an inlet portion or area 76 at the sealing area 62. The inlet 20, as discussed above, may allow a fluid to generally flow in the direction of arrow 18 from the ventricle 24 into the inlet area 76 of the valve assembly 50. When the valve member 68 is not sealed into the sealing surface 64, fluid may flow through and past the valve sealing area 62 through a valve volume 78 and out an outlet 82. The valve volume 78 is a reservoir volume of the valve assembly 50. The outlet 82 may be integrally formed and/or connected to the outlet catheter 32, such that the fluid may flow generally in the direction of arrow 18 through the outlet catheter 32, as discussed above. Accordingly, the valve assembly 50 may allow for flow of the CSF through the valve volume 78 and/or stop flow by sealing the sealing member 68 onto the sealing surface 64, as discussed above and further herein.

The valve assembly 50 may include the valve body 54 and/or valve body portions 54, 58 into a sealed configuration such that the internal volume 78 of the valve assembly 50 allows for a control of flow through the valve assembly 50. The valve assembly may further adjust or change a pressure of the sealing member 68 against the sealing surface 64. In various embodiments, therefore, the sealing member 68 may be biased generally in the direction of an arrow 86 into the sealing surface 64. A pressure applied through the inlet area or volume 76 may generally be in a direction of an arrow 88 opposite the arrow 86. The sealing member 68 may be removed or moved away from the sealing surface 64 to allow the flow through the outlet 82. As discussed further herein, the biasing pressure or the sealing pressure or force generally in the direction of arrow 86 may be adjusted and/or selected based upon various factors and parameters to select an opening or cracking pressure to allow the CFS to flow through the valve assembly 50, generally in the direction of arrow 18.

The valve assembly 50 further includes a power source 94, which may include one or more batteries. The power source 94 may store power for operating or powering a control assembly or portion 98. The control assembly 98 may include various portions, such as those discussed further herein, for controlling or manipulating the sealing member 68 relative to the sealing portion or ring 64. In various embodiments, the control assembly 98 may be sealed relative to the valve volume 68 by a sealing assembly or internal sealing assembly 102. The sealing assembly 102 may include various portions such as an outer or an external sealing ring or member 106 that may seat or seal against a wall 110 having an upper surface 114 that may seal against a lower surface 118 of the control assembly portion 98. The internal sealing portion 102 may further include a sealing membrane 126 that may span an area within the sealing member or portion 106. The sealing portion 106 may further include an upper surface 128 that may seal against an inner or lower surface 134 of the valve body or cap 54. Thus, the valve volume 78 may be sealed from the control assembly 98 and/or the battery 94. The valve assembly 50 may operate or include electronic components in the control assembly 98 regardless of the material that flows through the valve volume 78.

The control assembly portion 98, as discussed above, may include a seal or engaging wall 114. The sealing wall 114 may extend from a selected assembly or surface, such as a printed circuit board (PCB) including a glass PCB 140. The PCB 140 may include a selected component and/or include or encapsulate selected components such as a coil or antenna assembly 144. The antenna assembly 144 may be used for various purposes, such as communication with an external controller or programmer 148 (FIG. 1). Further, the antenna assembly 144 may be used to assist in recharging (e.g. inductive charging) the power source 94 such as with a near filed charging assembly end or inductive assembly. Thus, the antenna 144 may be used for communication with a selected component, such as the programmer 148 and/or for recharging the power source 94.

The antenna assembly 144 may be used for communication with the control assembly 98 and/or between with the controller or programmer 148. The control assembly 98 may include various components that may be used to store and/or execute instructions. The control assembly 98, for example, may include various components for operation of the valve assembly 50 to control a flow through the shunt assembly 10.

For example, the control assembly 98 may include a processing unit or module 150 may communicate with a selected assembly, such as a microelectromechanical system (MEMS) 154 to control various components thereon for operation of the valve assembly 50. The controls may operate to move the sealing member 68 into the sealing ring 64. The control assembly 98 may further include a memory portion, such as included with the processor 150 and/or separate from the processor 150. In addition, the control assembly 98 may include various components such as a signal generator 158 that may generate a signal, such as the transmission with the antenna 144. Further the control assembly or components 98 may include a capacitor and/or other electronic component 162 and an oscillator assembly 166.

The various components of the control assembly 98 may be provided for operation or assembly of the valve assembly 50, as discussed further herein. Generally, the control assembly 98 may include one or more processor systems that may receive feedback and/or instructions for selecting or providing a cracking or opening pressure of the sealing member 68 from the sealing ring 64. Accordingly, the processor 150 may be provided to execute selected instructions in various other appropriate or selected electronic components may be provided to operate the valve assembly 50. Accordingly, the above and herein described components may be exemplary and alternative and/or additional components may be provided to operate the valve assembly 50.

According to various embodiments, the MEMS 154 may include one or more components to selectively control the valve assembly 50 such as by applying a biasing pressure or force generally in the direction of arrow 86 of the sealing member 68 onto the sealing ring 64. With continuing reference to FIGS. 2 and 3, and additional reference to FIG. 4, the MEMS assembly 154 may include one or more actuators 180 formed on a substrate 184. The substrate 184 and the actuators 180 may be formed in any appropriate manner, such as those generally known in the art. Such actuators and manufacturing techniques may include actuators such as those produced or developed by Sandia National Labs. Other examples include sensors that can also act as actuators such as MEMs microphones including the MP34DT05 and MP34DT06J microphones sold by STMicroelectronics.

Figure 4:
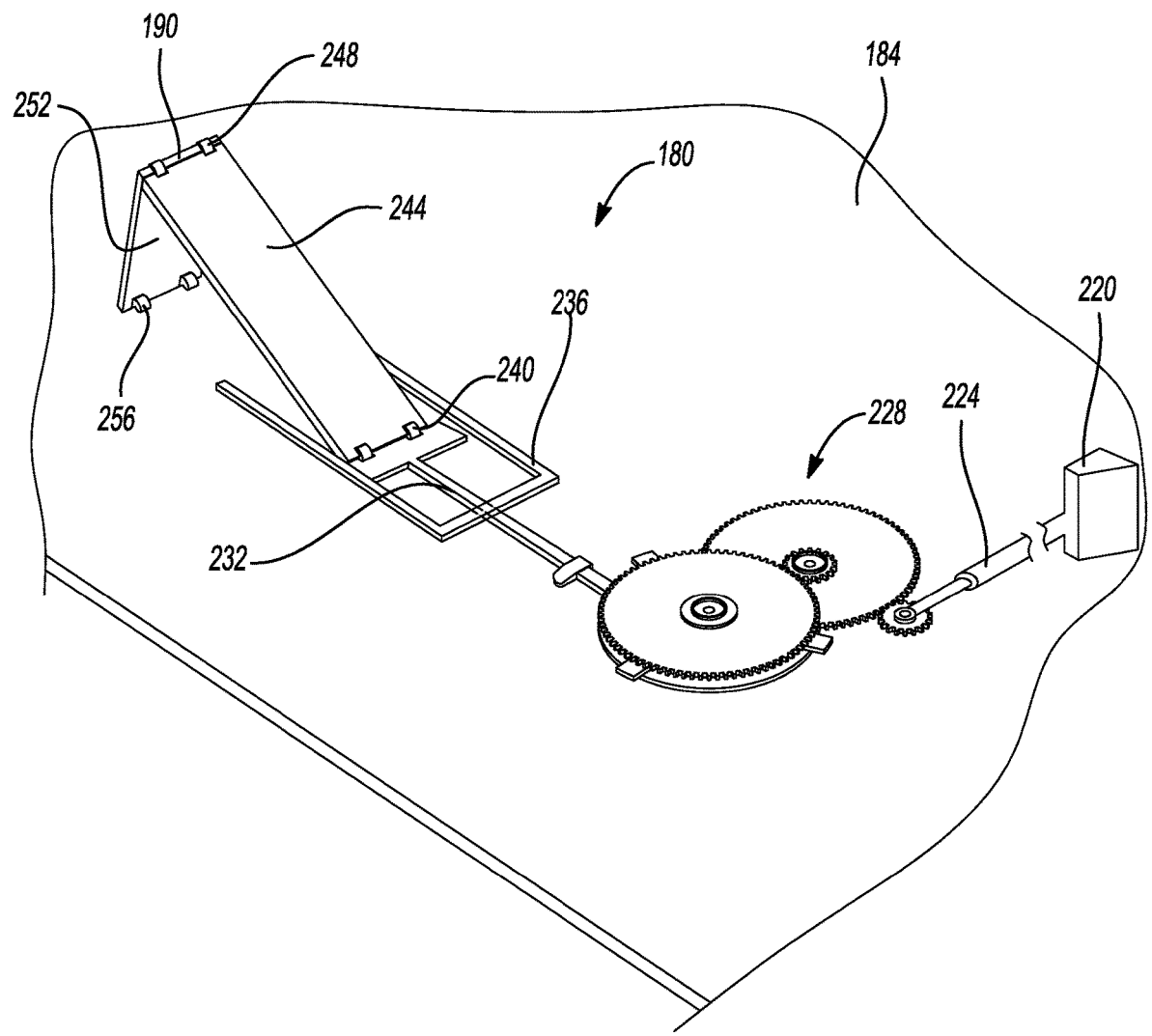
FIG. 4 is a detailed view of an actuator, according to various embodiments.
Figure 5A:
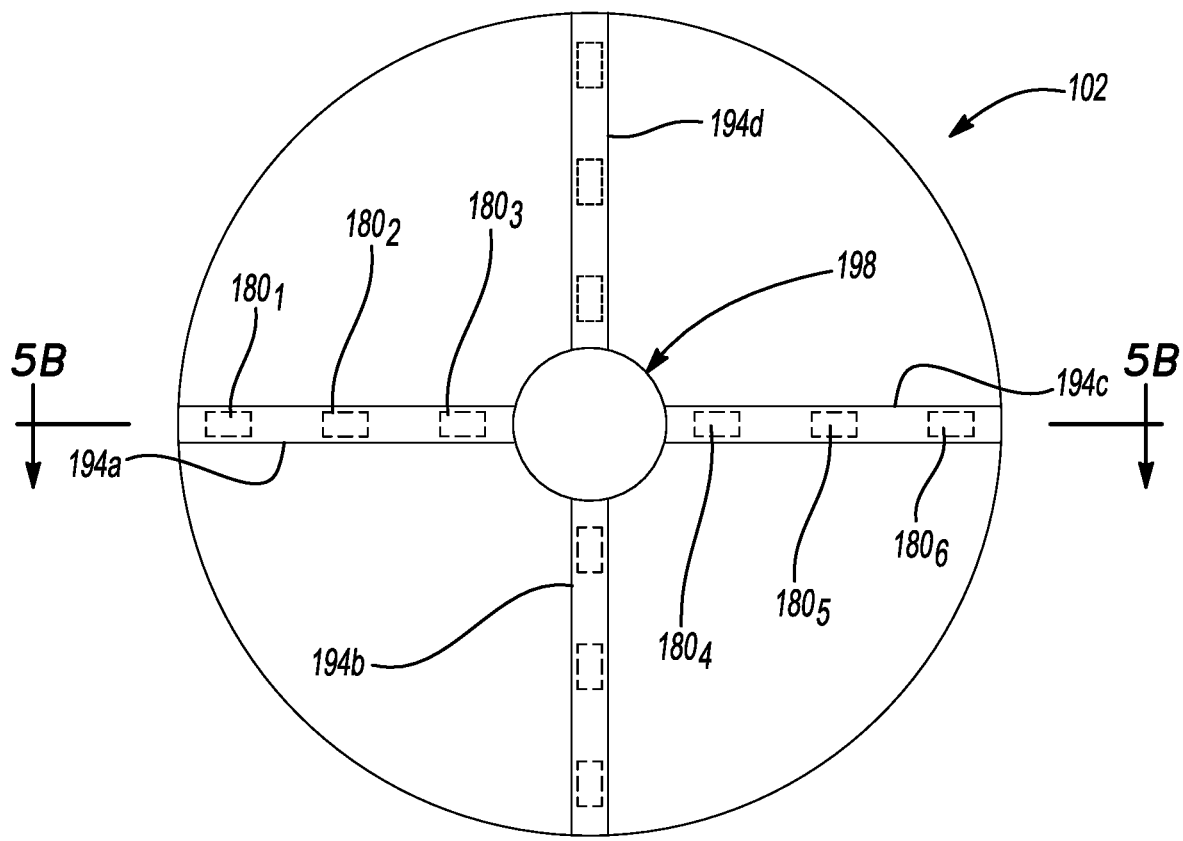
FIG. 5A is a top plan view of a support assembly.
Figure 5B:
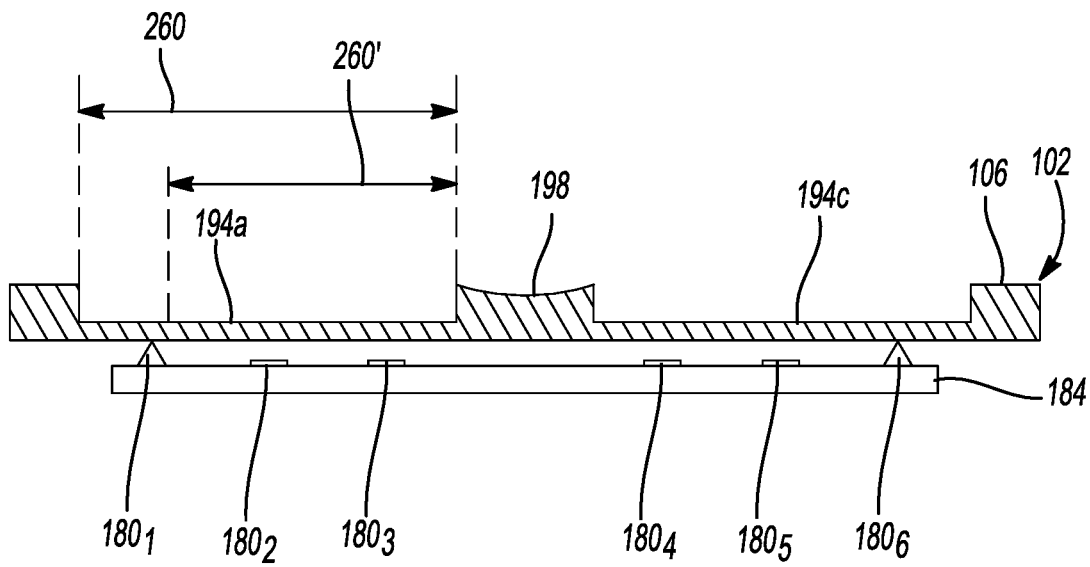
FIG. 5B is a cross-section taken along lines 5B-5B of FIG. 5A.

The actuators 180 may be actuated at least between two positions, such as a flat or substantially planar position and a raised or engaged positions, as illustrated in FIG. 4 and FIG. 5B. In the raised position, the actuator may include an engaging or contacting surface or portion 190 that may engage a cantilever or supporting member 194. The valve assembly 50 may include a selected number of cantilever members 194, such as four cantilever 194 formed in a cruciform, as illustrated in FIG. 2. The cantilevers 194 may be individually identified as 194a, 194b, 194c, and 194d. The supports 194 may be connected, such as cantilevered, at one end to the sealing member 106. The sealing member 106 may be further supported in the valve assembly 50, while the arms 194 extend therefrom to interact with a valve support or support member 198 that is configured to support or hold the sealing member 68. The valve support 198 and/or the valve member 68 may otherwise be unsupported within the valve assembly 50. The flexible assembly 126 may provide some support, but the arms 194 may also assist in supporting the flexible assembly 126. It is understood, however, that the arms 194 need not be cantilevered from the sealing member 106 and may otherwise be supported from the substrate 184, the control assembly wall 110, or other appropriate position.

In various embodiments, therefore, each of the cantilever portions 194 may be engaged by one or more of the actuators 180, such as with the contacting portion 190. Each of the actuators, as discussed above and herein, may also be individually identified by a lowercase letter a, b, c, or d. Therefore, the selected actuator may engage the selected support arm 194 to apply a pressure to the valve support or support member 198 that supports or holds the sealing member 68 and/or directly to the sealing member 68.

The support member 198 may support the sealing member 60 in a selected position relative to the sealing ring 64. The support member 198 may include an external wall 202 that forms or defines an internal surface 206 that may be complimentary or near the shape of the sealing member 68. As the sealing surface 64 may also compliment or engage the sealing member 68 the support member 198 may also engage the sealing member 68 to seal the passage or volume 78 relative to the flow of the fluid though the valve assembly 50. Accordingly, the support member 198 may engage and hold the sealing member 60 at a selected position and apply a force generally in the direction of the arrow 86 to select or control a flow of the fluid through the valve assembly 50.

The cantilever arms 194 may extend from the sealing ring or wall 106 toward the support member 198. Accordingly, the cantilever arms 194 may hold or support the support member 198 relative to the sealing wall 106 and/or the control assembly wall 110. As illustrated in FIG. 3, the valve assembly 50 including the control assembly 98 and the sealing assembly 102 may engage or seal the sealing member 68 within the valve assembly 50 and the various control components of the control assembly 98, as discussed above.

Further, extending between the cantilever arms 194 may be the sealing or flexible assembly 126. The flexible assembly 126 may seal the valve volume 78 from the control components 98, as discussed above. Further, the flexible portion 126 may move with the cantilever arms 194 to maintain the seal of the volume 78 relative to the electronic components 98 and other portions of the valve assembly, such as relative to the external sealing ring or wall 106.

In various embodiments, for example, the actuators 180 may move the cantilever arms 194 generally in the direction of arrow 86. In other words, the actuator members 180 may move the sealing member 68 to engage with the sealing surface 64. In various other embodiments, however, the sealing member 68 may be assembled into the valve assembly 50 such that the sealing member contacts the sealing surface 64. The actuators 180 may apply a force to increase a biasing force of the sealing member 68 onto the sealing surfaces 64 such as a force generally in the direction of the opening direction 88 needs to be increased above or greater than the force created by the cantilever arms 194. Accordingly, the actuators 180 may be operated or moved into an actuated or contacting position to change or alter an opening pressure or force on the valve assembly, such as to move the sealing member 68 generally in the direction of arrow 88 to open the valve assembly 50. Accordingly, the actuators 180 may operate to move the sealing member 68 into the sealing surface 64 and/or increase the biasing force generally in the direction of arrow 86 to adjust an opening or cracking pressure of the valve assembly 50.

As illustrated in the Figures, the actuators 180, therefore, may generally be moved or operated to move in the direction of arrow 86 and/or in the direction of arrow 88 by a selected electromechanical system, including portions generally understood by those skilled in the art. For example, a power or driving portion 220 may be formed or placed on the electronics component 98. The driving component 220 may be interconnected with various linkages, such as a first linkage 224 to one or more gears or gear assemblies 228. The gear assemblies 228 may rotate when powered by the driver 220. The gear assembly 228 may transfer, increase or decrease a power ratio, or change the direction of a motor for force. The motor force may move a drive or pushing arm 232 that may be held or moved relative to a rail or rail assembly 236.

The drive arm 232 may be hingedly connected by one or more hinges 240 to a first member or support member 244 of the actuator 180. The first support member 244 may be hingedly connected by a second hinge portion or assembly 248 to a second support member 252. The two support members 244, 252 may interact to form the actuator 180, as discussed further herein. The second support member 252 may also be hingedly connected by a third hinge portion or assembly 256 to the substrate 184.

As is generally understood by one skilled in the art, the actuator assembly 180 may be formed on the substrate 184 in any appropriate manner. For example, a MEMS system or machine, such as the actuator 180, may be formed by selected appropriate techniques such as etching (e.g. wet or dry etching), electrical discharge machining (EDM), molding, plating, and the like. As is generally understood by one skilled in the art the various manufacturing techniques may be used to form the various components of the MEMS system, such as the actuator 180. The actuator 180 may then be incorporated into other components and/or with other components, such as with the processor 150 for operation according to selected techniques and/or instructions.

With continuing reference to FIGS. 3 and 4, and additional reference to FIGS. 5A and 5B, the actuator 180 may be operated, such as according to instructions executed by the processor 150, to engage one or more of the cantilever or support arms 194. The actuators 180 may be moved to the actuated or engaging position, as illustrated in FIG. 4. In the engaged position, the engaging portion 190 may engage or contact the support or cantilever arm 194. As illustrated in FIG. 4, according to various embodiments, the engaging portion 190 may be supported by the second engaging or supporting member 252 relative to or against the first supporting 244. The first supporting member 244 may be moved to push against, and therefore cause, the second support member 252 to move generally in a vertical direction, such as away from the substrate 184 generally in the direction of arrow 86. Upon movement or in the engaging position, the actuator 180 may engage the cantilever arm 194.

With reference to FIG. 5A and FIG. 5B, the substrate 184 may be positioned relative to or near the support structure or portion 102. In various embodiments, for example, the two support cantilever members 194a, 194c may extend from the outer or extend the wall 106 toward the valve support member 198. The support members 194a, 194c may generally be formed to be substantially rigid and support the support member 198 at a selected distance from the external wall 106. Generally, the support arms 194a, 194c, or any of the support arms 194 may be substantially the same length 260 from the internal wall 106 to the support member 198, and/or to a center of the support member 198.

When the sealing member 68 is positioned in the support member 198 and engages the sealing surface 64, an incoming force, such as generally in the direction of arrow 88, may deflect or move the sealing member 68 away from the sealing surface 64 by deflecting or moving the support members 194 also generally in the direction of arrow 88. Therefore, the force applied by the support members 194 may be overcome by an incoming force, such as a hydraulic force caused by an inflow of fluid. Further, the opening force may be set by the distance 260, form or material of the support members 194, or other appropriate features. For example, a size, thickness, rigidity, material selection, or the like may be made to set or select an initial force required to move the sealing member 68 away from the sealing surface 64.

During operation of the flow control valve assembly 50, however, the actuators 180 may be selectively operated to engage the support members 194. In various embodiments, a plurality of the actuators may be provided. In various embodiments, for example, three actuators may be positioned between or in the distance 260. For example, as illustrated in FIG. 5A between the substrate 184 and the support member 194a may be three of the actuators 1801, 1802, and 1803. Further, between the substrate 184 and the support member 194c may be three additional actuators 1804, 1805, and 1806. During operation, any one or more of the actuators 180 may be actuated to contact the respective supports 194. Further, in the various manufacturing techniques, each of the actuators may be individually and separately operated or actuated to contact the supports 194. It is understood that the supports 194b and 194d also include respective actuators 180, which are not discussed specifically here but are understood to operate in a generally similar manner.

During operation of the valve assembly 50, for example, the outermost or first actuators for both of the support arms 194a, 194c may be operated. Accordingly, the actuator 1801 and 1806 may be operated to extend from the substrate 184 and contact the respective support members 194a, 194c. As illustrated in FIG. 4, the actuator 180 may extend from the substrate and the contact area 190 may contact the supports 194. Accordingly, the supports 194 may be further stiffened or have the distance 260 effectively shortened, such as to a distance 260'. By stiffening the support member 194, and/or further supporting the support member 194 relative to the substrate 184, the force required in the direction of arrow 88 to move or unseat the sealing member 68 from the sealing surface 64 may be increased. The amount of force may be generally known and calibrated relative to or per the distance 260 and/or the distance 260', the selected number of the actuators 180 actuated to engage the respective support members 194, or other appropriate mechanisms. Accordingly actuation of the actuators 180 may be made to contact the support members 194 and increase the opening pressure of the valve assembly 50.

According to various embodiments, for example, the valve assembly 50 may be operated to select an opening pressure or force to unseal the sealing member 68. Selected feedback may be provided to select an opening pressure. The opening pressure may be selected or set. Further the opening pressure or force may be based upon a selected or measured input pressure.

As discussed above, the various actuators 180, according to various embodiments and exemplary illustrated as the actuators that may be formed as an "A" frame subassembly are illustrated. These actuators may contact the support members 194 to generate or allow the sealing member 68 to remain seated in or against the sealing surface 64 and/or move away from the sealing surface 64.

The valve assembly 50, as illustrated in FIG. 2 and FIG. 3, may further include a pressure sensor assembly 290. The pressure sensor 290 may be incorporated into the support member 198 such as include with the support member 198 to engage or sensor a pressure on the support member 198. The pressure sensor 290 may also be another appropriate portion. In various embodiments, the pressure sensor 290 may include or incorporate the sealing membrane 126 and/or the supports 194. For example, the pressure sensor 290 may be any appropriate pressure sensor such as a piezo-resistive pressure sensor and the sealing portion or member 126 may act as a component thereof. Appropriate piezo-resistive pressure sensors include pressure transducers, such as those sold by Koninklijke Philips N.V., having a pace of business USA, including and/or similar to the pressure sensor included in the CPJ84022 pressure transducer assembly sold by Koninklijke Philips N.V. Other examples include the MPX5010/MPXV5010G/MP3V5010 series sensors sold by NXP Semiconductors. The pressure sensors 290 may sense a pressure of the sealing member 68 against the valve seal 198. The pressure sensed with the pressure sensor 290 may be based upon an incoming pressure such as through the inlet 20. Accordingly, the pressure through the inlet 20 may be based upon the pressure of the CFS flowing into the inlet 20 and/or into the valve assembly 50. The pressure sensor 290 may transmit a signal to the processor 150 in an appropriate manner, such as with a wired connection (e.g. a trace through the support assembly 102 to the electronics assembly 98), wirelessly, or combinations thereof. The signal may be measured over time and may, therefore, be measured as an absolute instantaneous pressure, a change in pressure, or other appropriate determination of pressure sensed at the pressure sensor 290.

The valve assembly 50 may be operated based upon the signal from the pressure sensor 290. For example, a selected threshold change in pressure, a selected measured absolute or instantaneous pressure, or any other appropriate pressure determination may be used to operate the valve assembly 50. As discussed further herein, for example, at a selected instantaneous pressure (e.g. a pressure above a selected threshold) a certain number of the actuators 180 may be relaxed or made inactive to allow for a flow of the CSF more easily (such as by lowering the opening force) though the valve assembly 50. Further, at a selected instantaneous pressure (e.g. at a pressure below a selected threshold) a selected number of the actuators 180 may be operated to increase an opening pressure required to move the sealing member 68 from the sealing surface 64. Thus, a selected volume or pressure of CSF may be maintained within the ventricle 24 of the subject 14 according to selected parameters, such as those identified and programmed by a user, such as with the programmer 148.

As discussed above, the valve assembly 50 can include various components, including those as situated and discussed above. With continuing reference to the above figures, and further reference to FIG. 6, the valve assembly 50 may include various components that may operate, as discussed further herein. Generally, the valve assembly 50 may include the processor or control assembly 150. As discussed above, the processor module or control module may be used to evaluate various inputs to control operation of components of the valve assembly 50. The inputs may also be various inputs such as sensor inputs or external inputs.

In various embodiments, the programmer 148 may be operated by a user, such as a clinician or a surgeon, to select a set point or selected value for one or more parameters of or relative to the valve assembly 50. In various embodiments, the set point may be a pressure set point, such as a pressure experience at or on the valve member at the inlet, sealing area, or seat 62. The selected set point may be one or more discrete pressure set points that may be selected directly and/or from a list by the user. As discussed above, the programmer 148 may include various inputs or input portions such as buttons or a touch screen 149 and/or a display 151. The user may therefore provide various inputs and/or selections with the programmer 148.

Figure 6:
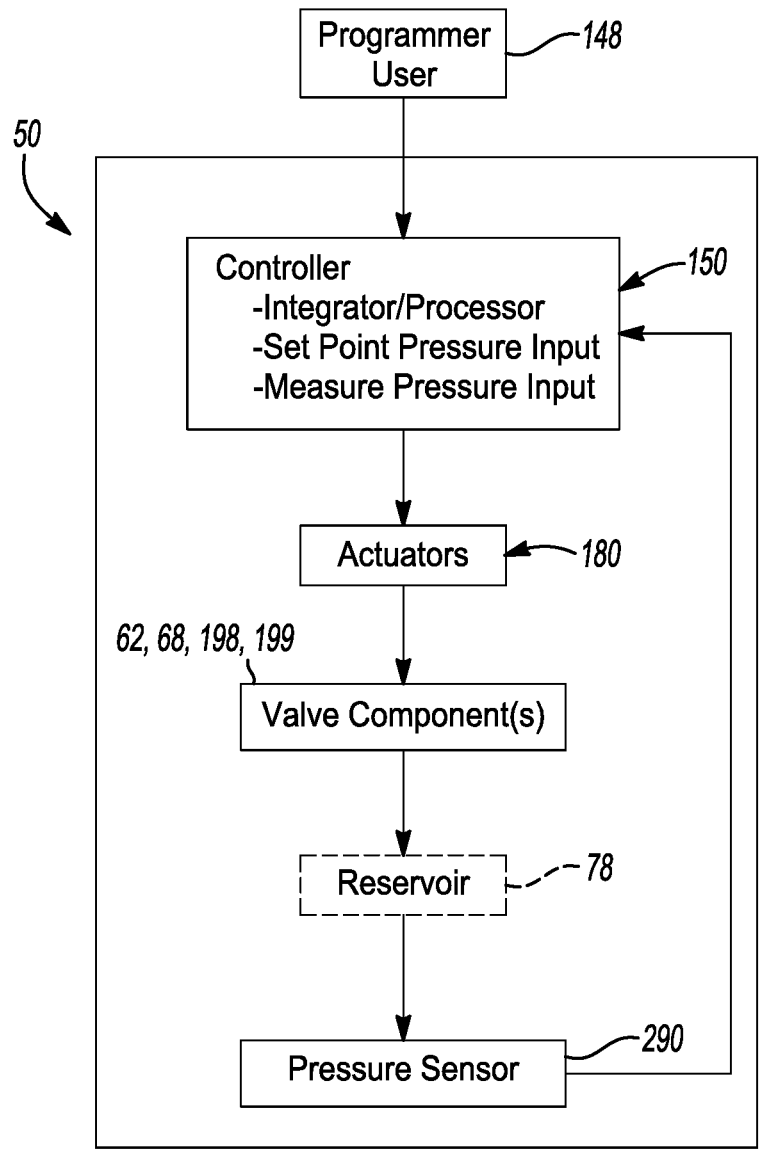
FIG. 6 is a schematic illustration of a valve assembly, according to various embodiments.

The selections by the user from the programmer 148 may then be transmitted to the controller 150, as illustrated in FIG. 6. The transmission may be in any appropriate manner such as a wireless transmission, wired transmission, or other type of transmission. As discussed above, the valve assembly 50 may include one or more portions, such as the antenna 144. Accordingly the programmer 148 may wirelessly transmit a signal to the controller 150 through the antenna 144. Regardless the programmer 148 may be used to determine or select a set point, such as a pressure set point for the valve assembly 50. It is understood that other appropriate inputs may be provided to the controller 150 to select or determine a set point, such as a pressure set point.

As discussed above, the valve assembly 50 may include the pressure sensor 290 that may be incorporated or positioned in selected portions of the valve assembly 50, such as within or near the reservoir 78. The pressure sensor 290 may measure a pressure within the reservoir 78 or other selected portion of the valve assembly 50. The pressure sensor may then transmit a signal to the controller 150. As discussed above the signal may be transmitted wirelessly and/or via the electronics component of the valve assembly 50. Nevertheless, the pressure sensor 290 may measure or sense a pressure and transmit a selected signal related to the measured pressure to the controller 150.

The controller 150 may further include an integrator which may be included in the processor module, to integrate or compare the set point input to a measured pressure input. The controller 150 may then integrate or compare the received measured pressure input to the set point pressure input. Based upon the comparison, the controller 150 may then determine to change or alter a configuration of the valve assembly 50. As discussed above, the valve assembly 50 may be operated to increase or decrease a cracking or opening pressure of the valve components to increase a flow or decrease a flow through the valve assembly. Accordingly, the controller may, if determined based upon a comparison, transmit a signal, also referred to as an actuator signal, to the actuators 180.

The actuators 180, upon receiving a selected signal from the controller 150, may then either activate or deactivate (e.g. move to an inactive position), or remain the in the same position. As discussed above, the actuators 180 may activate or raise (i.e. FIG. 4) to change or increase a cracking or opening pressure of the valve assembly 50. When raised, the actuator contacts the support arm 194. The actuators 180 may deactivate or lower to decrease an opening or cracking pressure of the valve assembly 50. When lowered the actuator contacts the support arm 194. Accordingly, the actuators 180 may operate or move based upon a signal from the controller 150 in light of the measured or sensed pressure from the pressure sensor 290.

The valve components, such as the valve member 68, the sealing areas 64, and/or the ball or valve support 198, may then be altered or effected by the actuators 180, as discussed above. The actuators 180 may increase or decrease an effective length of the supports 194 to change the force (e.g. biasing) on the valve seat 198. Thus, the valve may change its configuration and opening pressure for operation of the valve assembly 50.

The valve assembly 50, according to various embodiments, may include the components as illustrated in FIG. 6, to effect a therapy for the subject 14. A user may select a pressure set point, such as via the programmer 148, which is transmitted to the controller 150. The controller 150 may then receive the input from the set point and measure or sense pressure from the pressure sensor 290 for operation of the valve assembly 50.

In various embodiments, the set points may include a selected number of discrete pressure settings, such as about 20 discrete pressure settings at set or selected intervals between about 20 millimeters (mm) of water (about 0.02 pounds per square inch (PSI)) to about 400 mm of water (about 0.6 PSI). In various embodiments, for example, the discrete pressure settings may be at about 20 mm of water between 20 mm of water and 400 mm of water. The user may select from a selected number of discrete settings with the programmer 148 that may be displayed on the display 150. It is further understood, however, that selected set points may be made by the user that may be then transmitted to the controller 150 for operation and control of the valve assembly 50.

With continuing reference to FIG. 6 and additional reference to FIG. 7, a method or operation of the valve assembly 50 is illustrated in the flow chart 300. The method 300 may begin at start block 310. The start block 310 may include appropriate steps or portions, such as initiating operation of the valve assembly 50. It is understood that the start block 310 may further include and/or follow other operations such as diagnosis of the subject 14, determination of a selected therapy, implantation of the valve assembly 50, selection of various features, or the like. Nevertheless, the process 300 may begin in start block 310. After the start 310, the valve assembly 50, such as the controller 150, may receive an input. As discussed above, the programmer 148 or other appropriate portion may be used to select and transmit a signal to the valve assembly 50. The programmer 148 may be operated by a selected user to transmit an input or signal to the valve assembly 50.

The received input in block 320 may be any appropriate inputs such as a pressure input set point. As discussed above, the user may select one or more pressure set points and these may be received by the controller 150. Other appropriate inputs may also include a flow rate that may be achieved or selected through the valve assembly 50. Further, a specific actuator configuration may also be determined. As discussed above, the actuators 180 may be used to select or achieve a selected distance 260 of the support 194. The specific configuration may be determined by the user and provided as an input that may be received by the controller 150. Nevertheless, as discussed above, the input may be a pressure set point and the controller 150 may select the actuators 180 to activate based upon a predetermined configuration (e.g. a factory calibration). Nevertheless, the input may be received in block 320 at the controller 150. In various embodiments, the input may also include a start or stop command for the valve assembly 50.

The received input at the controller 150 may be used in combination with a sensed or measured parameter in block 330. For example, the sensed or measured parameter in block 330 may relate to or be regarding the received input from block 320. For example, as discussed above, the pressure sensor 290 may sense a pressure in the reservoir 78, such as at the valve member 68, of the valve assembly 50. The parameter measured may also include a flow rate, or other appropriate measurement. In various embodiments, such as those discussed further herein, include measuring a pressure in block 330 with the pressure sensor 290. The sensed or measured pressure may then be transmitted with a signal from the pressure sensor 290 in block 340. The signal may be transmitted to the controller 150 for comparison to the received input in block 350.

As discussed above, the controller 150 may include various components, such as an integrator, processor module, or the like for comparison of the received input to the transmitted signal. In various embodiments the received input may include a pressure set point from the programmer 148. The pressure set point may then be compared to the signal from the pressure sensor transmitted in block 340 and compared in block 350. The signal may include a selected signal, such as an analog or digital signal that may be compared to the received input from block 320. The appropriate comparison, may be any appropriate comparison, to allow for a determination of whether the valve assembly 50 is operating at the selected set point. Accordingly, a decision may then be made by the controller 150 of whether the transmitted signal matches the received set point in block 360.

The decision block 360 may be made based upon the comparison block 350. Accordingly, the selected user may transmit a set point in block 320 which may be compared in block 350 to a measured parameter in block 330.

If the decision block 360 determines that the transmitted signal matches the received input a YES path 370 may be followed. The YES path 370 may be returning to either receiving the input in block 320 and/or sensing a measured parameter in block 330. In various embodiments, therefore, the method 300 may be a loop process where the parameter is continually measured in block 320 and compared in block 350. The decision block 360 may be then used to determine whether the operation of the valve assembly 50 needs to be altered. A periodic check, such as over a selected period of time, including every hour, every 24 hours, or the like may be made to determine whether the controller 150 has received an additional input from the user in block 320. Accordingly, a selected additional or new input from the user to the controller 150 may alter or change the operation of the method 300. For example, the user may determine to stop operation of the valve assembly 50, such as for maintenance, removal, or the like.

If the decision block 350 determines that the transmitted signal from block 340 does not match the received input from block 320, a NO path 380 may be followed. The NO path 380 may include transmission of a signal to activate or deactivate actuators in optional block 390. The actuators, as discussed above, may alter the valve assembly in block 400. The actuators 180 may alter or change various valve components, such as the sealing portion or member 126, the support 190, or the like. The transmission of a signal to activate or deactivate actuators in block 390 may be one selected operation of the valve assembly 50 to alter or change the valve assembly 50 to attempt to achieve the selected set point or input from the user in block 320. Accordingly, when the NO path 380 is followed, altering the valve assembly in block 400 may be performed. Appropriate alterations may include activating or deactivating one or more of the actuators, such as by transmission of the signal in block 390.

After altering the valve assembly in block 400, a continuation of sensing or measuring a parameter in block 330 may be followed, as discussed above when following the YES path 370. Again, a periodic or selected check of an input from the user in block 320 may also be made, such as over a selected or set period of time.

Accordingly, the valve assembly 50 may be operated according to the method 300 for controlling the pressure and/or flow rate through the valve assembly 50. The valve assembly 50 may receive a signal, such as at the controller 150. The signal may be from the user, such as through the programmer 148, to control or select an operation of the valve assembly 50. The selection may include selection of a pressure set point, as discussed above. The method 300, therefore, may be used to operate or control the valve assembly 50, such as with the controller 150.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, graphic processing units (GPUs), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method of operating a flow and/or pressure regulating assembly for a hydrocephalus shunt system, the method comprising:
biasing a valve member in a closed position relative to a valve seat with an arm support member;
sensing a parameter relative to the valve member; and
operating a MEMS (microelectromechanical system) movable actuator formed from and on a substrate near the arm support member to be moved to an active position or moved an inactive position at a fixed location relative to the arm support member to effect a biasing force applied to the valve member.

2. The method of claim 1, further comprising:
selecting an effective support length of the arm support member to determine the biasing force on the valve member.

3. The method of claim 2, further comprising:
executing instructions with a controller to compare a sensed pressure applied to an inlet side of the valve member to determine the position of the actuator.

4. The method of claim 3, wherein operating the actuator in the active position includes decreasing a support length of the arm support member to increase the biasing force.

5. The method of claim 3, wherein operating the actuator in the inactive position includes increasing or maximizing a support length of the arm support member to decrease the biasing force.

6. The method of claim 1, further comprising:
selecting a set point for the parameter;
comparing the set point of the parameter to the sensed parameter; and
selecting a position of the actuator based on the comparison.

7. The method of claim 6, wherein the parameter is an inlet pressure.

8. The method of claim 7, further comprising:
receiving the selected set point; and
storing the set point.

9. The method of claim 7, further comprising:
executing instructions with a controller to perform the comparison;
transmitting an actuation signal to move the actuator to the active position to decrease a support length of the arm support member to increase the biasing force when the sensed parameter is less than the set point.

10. The method of claim 7, further comprising:
executing instructions with a controller to perform the comparison;
transmitting an actuation signal to move the actuator to the inactive position to increase a support length of the arm support member to decrease the biasing force when the sensed parameter is greater than the set point.

11. The method of claim 1, further comprising:
receiving a set point value for the parameter.

12. The method of claim 11, further comprising:
operating a controller to execute instructions to compare the sensed parameter and the received set point value.

13. The method of claim 12, wherein operating the actuator includes at least one of (i) moving the actuator from the active position to the inactive position, (ii) moving the actuator from the inactive position to the active position, or (iii) maintaining the actuator in a current active position or a current inactive position.

14. The method of claim 12, wherein operating the actuator includes forming the biasing force on the valve member based on the comparison.

15. The method of claim 1, wherein operating the actuator includes operating a plurality of movable actuators at fixed locations along the arm support member.

* * * * *

UNITED STATES PATENT AND TRADEMARK OFFICE
CERTIFICATE OF CORRECTION

PATENT NO. : 12,059,542 B2
APPLICATION NO. : 16/944466
DATED : August 13, 2024
INVENTOR(S) : Jemmy Sutanto et al.

Page 1 of 1

It is certified that error appears in the above-identified patent and that said Letters Patent is hereby corrected as shown below:

In the Specification

Column 1, Background, Line 24, Delete "hydrocephalous. Hydrocephalous" and insert --hydrocephalus. Hydrocephalus-- therefor Column 1, Background, Line 27, Delete "Hydrocephalous," and insert --Hydrocephalus,-- therefor Column 1, Background, Line 29, Delete "hydrocephalous" and insert --hydrocephalus-- therefor Column 1, Summary, Line 40, Delete "hydrocephalous." and insert --hydrocephalus.-- therefor Column 4, Detailed Description, Line 21, Delete "68" and insert --78-- therefor Column 6, Detailed Description, Line 2, Delete "60" and insert --68-- therefor Column 6, Detailed Description, Line 11, Delete "60" and insert --68-- therefor Column 8, Detailed Description, Lines 8-9, Delete "1801, 1802, and 1803." and insert --$180_1$, $180_2$, and $180_3$.-- therefor Column 8, Detailed Description, Line 11, Delete "1804, 1805, and 1806." and insert --$180_4$, $180_5$, and $180_6$.-- therefor Column 8, Detailed Description, Lines 22-23, Delete "1801 and 1806" and insert --$180_1$ and $180_6$-- therefor Signed and Sealed this
Twenty-second Day of April, 2025

Coke Morgan Stewart
*Acting Director of the United States Patent and Trademark Office*